US009651543B2

(12) United States Patent
Bruder et al.

(10) Patent No.: US 9,651,543 B2
(45) Date of Patent: May 16, 2017

(54) MALARIA ANTIGEN SCREENING METHOD

(71) Applicants: Joseph T. Bruder, Ijamsville, MD (US); Imre Kovesdi, Rockville, MD (US); Duncan L. McVey, Derwood, MD (US); Douglas E. Brough, Gaithersburg, MD (US); C. Richter King, Washington, DC (US); Denise Louise Doolan, Camp Hill (AU); Joao Carlos Aguair, Potomac, MD (US); Daniel John Carucci, Washington, DC (US); Martha Sedegah, Gaithersburg, MD (US); Walter R. Weiss, Bethesda, MD (US); Keith Limbach, Gaithersburg, MD (US)

(72) Inventors: Joseph T. Bruder, Ijamsville, MD (US); Imre Kovesdi, Rockville, MD (US); Duncan L. McVey, Derwood, MD (US); Douglas E. Brough, Gaithersburg, MD (US); C. Richter King, Washington, DC (US); Denise Louise Doolan, Camp Hill (AU); Joao Carlos Aguair, Potomac, MD (US); Daniel John Carucci, Washington, DC (US); Martha Sedegah, Gaithersburg, MD (US); Walter R. Weiss, Bethesda, MD (US); Keith Limbach, Gaithersburg, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 294 days.

(21) Appl. No.: 13/866,116

(22) Filed: Apr. 19, 2013

(65) Prior Publication Data

US 2014/0314809 A1 Oct. 23, 2014
US 2017/0082607 A9 Mar. 23, 2017

Related U.S. Application Data

(62) Division of application No. 11/513,439, filed on Aug. 25, 2006, now Pat. No. 8,450,055.

(60) Provisional application No. 60/713,001, filed on Aug. 31, 2005.

(51) Int. Cl.
G01N 33/50 (2006.01)
(52) U.S. Cl.
CPC ................ G01N 33/505 (2013.01)
(58) Field of Classification Search
None
See application file for complete search history.

(56) References Cited

U.S. PATENT DOCUMENTS

| 5,543,328 A | 8/1996 | McClelland |
| 5,559,099 A | 9/1996 | Wickham |
| 5,712,136 A | 1/1998 | Wickham |
| 5,731,190 A | 3/1998 | Wickham |
| 5,756,086 A | 5/1998 | McClelland |
| 5,770,442 A | 6/1998 | Wickham |
| 5,801,030 A | 9/1998 | McVey et al. |
| 5,837,511 A | 11/1998 | Falck-Pedersen |
| 5,846,782 A | 12/1998 | Wickham |
| 5,849,561 A | 12/1998 | Falck-Pedersen |
| 5,851,806 A | 12/1998 | Kovesdi |
| 5,962,311 A | 10/1999 | Wickham |
| 5,965,541 A | 10/1999 | Wickham |
| 5,994,106 A | 11/1999 | Kovesdi |
| 5,994,128 A | 11/1999 | Fallaux |
| 6,033,908 A | 3/2000 | Bout |
| 6,057,155 A | 5/2000 | Wickham |
| 6,127,175 A | 10/2000 | Vigne |
| 6,127,525 A | 10/2000 | Crystal |
| 6,153,435 A | 11/2000 | Crystal |
| 6,168,941 B1 | 1/2001 | Liu et al. |
| 6,329,190 B1 | 12/2001 | Wickham |
| 6,329,200 B1 | 12/2001 | McVey |
| 6,447,995 B1 | 9/2002 | Carrion et al. |
| 6,455,314 B1 | 9/2002 | Wickham |
| 6,465,253 B1 | 10/2002 | Wickham |
| 6,475,757 B2 | 11/2002 | McVey |
| 6,482,616 B1 | 11/2002 | Kovesdi |

(Continued)

FOREIGN PATENT DOCUMENTS

WO 98/53087 11/1998

OTHER PUBLICATIONS

Hill, AVS. Vaccines against malaria, Phil. Trans. R. Soc. B, 2011; 366: 2806-2814.*
Morin, et al. Recombinant adenovirus induces antibody response to hepatitis B virus surface antigen in hamsters. Proc. Natl. Acad. Sci. USA, 1987; 84: 4626-4630.*
Rodriguez, et al. Evaluation of a prime-boost vaccine schedule with distinct adenovirus vectors against malaria in rhesus monkeys. Vacc. 2009, 27: 6226-6233.*

Primary Examiner — Janet L Andres
Assistant Examiner — Stuart W Snyder
(74) Attorney, Agent, or Firm — Ning Yang; Albert M. Churilla; Diane P. Tso

(57) ABSTRACT

The invention provides a method of identifying an antigen from a pathogen or a disease antigen comprising the use of an adenoviral vector array comprising two or more different adenoviral vectors, wherein each adenoviral vector comprises a nucleic acid sequence encoding a different antigen of a pathogen. The adenoviral vectors are administered to antigen presenting cells (APCs) in vitro or to an animal in vivo. The immunogenicity of the antigen is measured by screening for an immune response from effector T lymphocytes in vitro and by screening for the absence of pathogen-induced disease onset in vivo.

6 Claims, No Drawings

(56) References Cited

U.S. PATENT DOCUMENTS 6,576,456 B2 6/2003 Wickham
6,649,407 B2 11/2003 Wickham
6,740,525 B2 5/2004 Roelvink
6,908,762 B2 6/2005 Kovesdi

* cited by examiner

MALARIA ANTIGEN SCREENING METHOD

CROSS-REFERENCE TO RELATED APPLICATIONS

This application is a divisional application of U.S. patent application Ser. No. 11/513,439 (now allowed), filed on Aug. 25, 2006, which claims priority to U.S. Provisional application 60/713,001 filed on Aug. 31, 2005.

STATEMENT REGARDING FEDERALLY SPONSORED RESEARCH AND DEVELOPMENT

This invention was made in part with Government support under Cooperative Research and Development Agreement (CRADA) Number NMR-04-1869, and amendments thereto, executed between GenVec, Inc. and the Naval Medical Research Center (NMRC). The Government may have certain rights in this invention.

REFERENCE TO SEQUENCE LISTING

A sequence listing is provided in paper form and as in computer readable form. I hereby state that the information recorded in computer readable form is identical to the written sequence listing.

BACKGROUND OF THE INVENTION

Malaria is one of the most devastating parasitic diseases affecting humans. Indeed, 41% of the world's population lives in areas where malaria is transmitted (e.g., parts of Africa, Asia, the Middle East, Central and South America, Hispaniola, and Oceania). The World Health Organization (WHO) and the Centers for Disease Control (CDC) estimate that malaria infects 300-500 million people and kills 700,000-3 million people annually, with the majority of deaths occurring in children in sub-Saharan Africa. Malaria also is a major health concern to U.S. military personnel deployed to tropical regions of the world. For example, in August 2003, 28% of the 26$^{th}$ Marine Expeditionary Unit and Joint Task Force briefly deployed to Monrovia, Liberia, were infected with the malaria parasite *Plasmodium falciparum*. In addition, one 157-man Marine Expeditionary Unit sustained a 44% malaria casualty rate over a 12-day period while stationed at Robert International Airport in Monrovia. In all conflicts during the past century conducted in malaria endemic areas, malaria has been the leading cause of casualties, exceeding enemy-inflicted casualties in its impact on "person-days" lost from duty.

To combat malaria during U.S. military operations, preventive drugs, insect repellants, and barriers have been used with some success, but developing drug resistance by the malaria parasite and insecticide resistance by mosquito vectors has limited the efficacy of these agents. Moreover, the logistical burden and side effects associated with the use of these agents often is associated with high non-compliance rates. Vaccines are the most cost effective and efficient therapeutic interventions for infectious diseases. In this regard, vaccination has the advantage of administration prior to military deployment and likely reduction in non-compliance risks. However, decades of research and development directed to a malaria vaccine have not proven successful. Recent efforts have focused on developing vaccines against several specific malaria genes and delivery vector systems including adenovirus, poxvirus, and plasmids. The current status of malaria vaccine development and clinical trials is reviewed in, for example, Graves and Gelband, *Cochrane Database Syst. Rev.*, 1: CD000129 (2003), Moore et al., *Lancet Infect. Dis.*, 2: 737-743 (2002), Carvalho et al., *Scand. J. Immunol.*, 56: 327-343 (2002), Moorthy and Hill, *Br. Med. Bull.*, 62: 59-72 (2002), Greenwood and Alonso, *Chem. Immunol.*, 80: 366-395 (2002), and Richie and Saul, *Nature*, 415: 694-701 (2002).

An unprecedented quantity of genomic data has emerged from the sequencing and functional genomic analysis of many disease-causing organisms, including malaria. Indeed, it has been determined that the parasite *Plasmodium falciparum* encodes an estimated 5,268 putative proteins (see Gardner et al., *Nature*, 419: 498-511 (2002)). This genetic information can be exploited for the systematic discovery of novel antigens for vaccine development. In the past, target antigens for genetic vaccines have been identified based mainly on their abundance in the pathogen of interest and their susceptibility to neutralization by antibodies generated in infected individuals and animal models. This approach has failed to yield effective vaccines against many of the most devastating infectious diseases. With regard to malaria, less than 5% of the *Plasmodium falciparum* genome is represented by antigens currently in clinical development. A vaccine containing a recombinant *P. falciparum* circumsporozoite protein (CSP) has been the most successful vaccine tested to date, providing a protective efficacy of 47-85% against experimental pathogen challenge (see, e.g., Stoute et al., *N. Engl. J. Med.*, 336: 86-91 (1997), Stoute et al., *J. Infect. Dis.*, 178: 1139-1144 (1998), and Kester et al., *J. Infect. Dis.*, 183: 640-647 (2001)) and pathogen challenge in the field (see Bojang et al., *Lancet*, 358: 1927-1934 (2001)). The protection afforded by this protein-based vaccine, however is short lived (3-8 weeks). Other recent efforts at developing a malaria vaccine have focused on several specific genes and their delivery using various different vector systems including adenovirus, poxvirus, and plasmid DNA. It is not apparent, however, whether these recombinant vaccines are effective against malaria, or if they encode the most potent protective antigens. It is clear that protective antigens do exist for the malaria pathogen *Plasmodium falciparum*, as evidenced by the ability of irradiated sporozoites to induce cellular immune responses in human subjects and robust sterile protection against parasite challenge (see, e.g., Nussenzweig and Nussenzweig, *Adv. Immunol.*, 45: 283-334 (1989), and Hoffman et al., *J. Infect. Dis.*, 185: 1155-1164 (2002)).

Thus, there remains a need for improved methods for identifying antigens that induce potent protective immunity against pathogen challenge. The invention provides such a method. This and other advantages of the invention will become apparent from the detailed description provided herein.

BRIEF SUMMARY OF THE INVENTION

The invention provides a method of identifying an antigen from a pathogen. The method comprises (a) preparing an adenoviral vector array comprising two or more different adenoviral vectors, wherein each adenoviral vector comprises a nucleic acid sequence encoding a different antigen of a pathogen, (b) contacting antigen presenting cells (APCs) with the adenoviral vector array, wherein each different adenoviral vector transduces an APC such that the nucleic acid sequences of the different adenoviral vectors are expressed and the different antigens are produced in the APCs, (c) incubating the APCs with effector T lymphocytes obtained from a mammal immunized with the pathogen, and (d) screening for an immune response from the effector T lymphocytes, wherein an immune response from an effector T lymphocyte contacting an APC indicates T lymphocyte recognition of the antigen produced by the APC, whereupon the antigen is identified.

The invention also provides a method of identifying an antigen from a pathogen, which method comprises (a) providing an adenoviral vector array comprising two or more different adenoviral vectors, wherein each adenoviral vector comprises a nucleic acid sequence encoding a different antigen of a pathogen, (b) administering each of the adenoviral vectors of the adenoviral vector array to a mammal, such that the nucleic acid sequence is expressed and the antigen is produced in the mammal, (c) infecting each mammal with the pathogen, and (d) screening the infected mammal for onset of a disease caused by the pathogen, wherein the absence in the infected mammal of a disease caused by the pathogen indicates that the adenoviral vector encodes an antigen of the pathogen, whereupon the antigen is identified.

The invention further provides a method of identifying a disease antigen, which method comprises (a) preparing an adenoviral vector array comprising two or more different adenoviral vectors, wherein each adenoviral vector comprises a nucleic acid sequence encoding a different disease antigen, (b) contacting APCs with the adenoviral vector array, wherein each different adenoviral vector transduces an APC such that the nucleic acid sequences of the different adenoviral vectors are expressed and the different antigens are produced in the APCs, (c) incubating the APCs with effector T lymphocytes obtained from a mammal affected by the disease, and (d) screening for an immune response from the effector T lymphocytes, wherein an immune response from an effector T lymphocyte contacting an APC indicates T lymphocyte recognition of the antigen produced by the APC, whereupon the disease antigen is identified.

DETAILED DESCRIPTION OF THE INVENTION

The invention provides a method of identifying an antigen from a pathogen comprising preparing an adenoviral vector array comprising two or more different adenoviral vectors. Adenovirus (Ad) is a 36 kb double-stranded DNA virus that efficiently transfers DNA in vivo to a variety of different target cell types. For use in the invention, the adenovirus is preferably made replication-deficient by deleting, in whole or in part, select genes required for viral replication. The expendable E3 region is also frequently deleted to allow additional room for a larger DNA insert. The vector can be produced in high titers and can efficiently transfer DNA to replicating and non-replicating cells. The newly transferred genetic information remains epi-chromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV ITRs and nucleic acid encoding the Rep protein incorporated into an adenoviral vector enables the adenoviral vector to integrate into a mammalian cell genome. Therefore, AAV-Ad chimeric vectors can be a desirable option for use in the invention.

Adenovirus from various origins, subtypes, or mixture of subtypes can be used as the source of the viral genome for the adenoviral vector. A non-human adenovirus (e.g., simian, avian, canine, ovine, or bovine adenoviruses) can be used to generate the adenoviral vector. Alternatively, a human adenovirus can be used as the source of the viral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 (i.e., Ad1 through Ad51) are available from the American Type Culture Collection (ATCC, Manassas, Va.). Preferably, in the context of the invention, the adenoviral vector is of human subgroup C, especially serotype 2 or even more desirably serotype 5. However, non-group C adenoviruses can be used to prepare adenoviral gene transfer vectors for delivery of gene products to host cells. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Application Publications WO 97/12986 and WO 98/53087.

The adenoviral vector can comprise a mixture of subtypes and thereby be a "chimeric" adenoviral vector. A chimeric adenoviral vector can comprise an adenoviral genome that is derived from two or more (e.g., 2, 3, 4, etc.) different adenovirus serotypes. In the context of the invention, a chimeric adenoviral vector can comprise approximately different or equal amounts of the genome of each of the two or more different adenovirus serotypes. When the chimeric adenoviral vector genome is comprised of the genomes of two different adenovirus serotypes, the chimeric adenoviral vector genome preferably comprises no more than about 70% (e.g., no more than about 65%, about 50%, or about 40%) of the genome of one of the adenovirus serotypes, with the remainder of the chimeric adenovirus genome being derived from the genome of the other adenovirus serotype. In one embodiment, the chimeric adenoviral vector can contain an adenoviral genome comprising a portion of a serotype 2 genome and a portion of a serotype 5 genome. For example, nucleotides 1-456 of such an adenoviral vector can be derived from a serotype 2 genome, while the remainder of the adenoviral genome can be derived from a serotype 5 genome.

The adenoviral vector of the invention can be replication-competent. For example, the adenoviral vector can have a mutation (e.g., a deletion, an insertion, or a substitution) in the adenoviral genome that does not inhibit viral replication in host cells. The adenoviral vector also can be conditionally replication-competent. Preferably, however, the adenoviral vector is replication-deficient in host cells.

By "replication-deficient" is meant that the adenoviral vector requires complementation of one or more regions of the adenoviral genome that are required for replication, as a result of, for example, a deficiency in at least one replication-essential gene function (i.e., such that the adenoviral vector does not replicate in typical host cells, especially those in a human patient that could be infected by the adenoviral vector in the course of the inventive method). A deficiency in a gene, gene function, gene, or genomic region, as used herein, is defined as a mutation or deletion of sufficient genetic material of the viral genome to obliterate or impair the function of the gene (e.g., such that the function of the gene product is reduced by at least about 2-fold, 5-fold, 10-fold, 20-fold, 30-fold, or 50-fold) whose nucleic acid sequence was mutated or deleted in whole or in part. Deletion of an entire gene region often is not required for disruption of a replication-essential gene function. However, for the purpose of providing sufficient space in the adenoviral genome for one or more transgenes, removal of a majority of a gene region may be desirable. While deletion of genetic material is preferred, mutation of genetic material by addition or substitution also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA 1 and/or VA-RNA-2).

The replication-deficient adenoviral vector desirably requires complementation of at least one replication-essential gene function of one or more regions of the adenoviral genome for viral replication. Preferably, the adenoviral vector requires complementation of at least one gene function of the E1A region, the E1B region, or the E4 region of the adenoviral genome required for viral replication (denoted an E1-deficient or E4-deficient adenoviral vector). In addition to a deficiency in the E1 region, the recombinant adenovirus also can have a mutation in the major late promoter (MLP), as discussed in International Patent Application Publication WO 00/00628. Most preferably, the adenoviral vector is deficient in at least one replication-essential gene function (desirably all replication-essential gene functions) of the E1 region and at least one gene function of the nonessential E3 region (e.g., an Xba I deletion of the E3 region) (denoted an E1/E3-deficient adenoviral vector). With respect to the E1 region, the adenoviral vector can be deficient in part or all of the E1A region and/or part or all of the E1B region, e.g., in at least one replication-essential gene function of each of the E1A and E1B regions, thus requiring complementation of the E1A region and the E1B region of the adenoviral genome for replication. The adenoviral vector also can require complementation of the E4 region of the adenoviral genome for replication, such as through a deficiency in one or more replication-essential gene functions of the E4 region.

When the adenoviral vector is E1-deficient, the adenoviral vector genome can comprise a deletion beginning at any nucleotide between nucleotides 335 to 375 (e.g., nucleotide 356) and ending at any nucleotide between nucleotides 3,310 to 3,350 (e.g., nucleotide 3,329) or even ending at any nucleotide between 3,490 and 3,530 (e.g., nucleotide 3,510) (based on the adenovirus serotype 5 genome). When E2A-deficient, the adenoviral vector genome can comprise a deletion beginning at any nucleotide between nucleotides 22,425 to 22,465 (e.g., nucleotide 22,443) and ending at any nucleotide between nucleotides 24,010 to 24,050 (e.g., nucleotide 24,032) (based on the adenovirus serotype 5 genome). When E3-deficient, the adenoviral vector genome can comprise a deletion beginning at any nucleotide between nucleotides 28,575 to 29,615 (e.g., nucleotide 28,593) and ending at any nucleotide between nucleotides 30,450 to 30,490 (e.g., nucleotide 30,470) (based on the adenovirus serotype 5 genome). When E4-deficient, the adenoviral vector genome can comprise a deletion beginning at, for example, any nucleotide between nucleotides 32,805 to 32,845 (e.g., nucleotide 32,826) and ending at, for example, any nucleotide between nucleotides 35,540 to 35,580 (e.g., nucleotide 35,561) (based on the adenovirus serotype 5 genome). The endpoints defining the deleted nucleotide portions can be difficult to precisely determine and typically will not significantly affect the nature of the adenoviral vector, i.e., each of the aforementioned nucleotide numbers can be +/−1, 2, 3, 4, 5, or even 10 or 20 nucleotides.

When the adenoviral vector is deficient in at least one replication-essential gene function in one region of the adenoviral genome (e.g., an E1- or E1/E3-deficient adenoviral vector), the adenoviral vector is referred to as "singly replication-deficient." A particularly preferred singly replication-deficient adenoviral vector is, for example, a replication-deficient adenoviral vector requiring, at most, complementation of the E1 region of the adenoviral genome, so as to propagate the adenoviral vector (e.g., to form adenoviral vector particles).

The adenoviral vector can be "multiply replication-deficient," meaning that the adenoviral vector is deficient in one or more replication-essential gene functions in each of two or more regions of the adenoviral genome, and requires complementation of those functions for replication. For example, the aforementioned E1-deficient or E1/E3-deficient adenoviral vector can be further deficient in at least one replication-essential gene function of the E4 region (denoted an E1/E4- or E1/E3/E4-deficient adenoviral vector), and/or the E2 region (denoted an E1/E2- or E1/E2/E3-deficient adenoviral vector), preferably the E2A region (denoted an E1/E2A- or E1/E2A/E3-deficient adenoviral vector). When the adenoviral vector is multiply replication-deficient, the deficiencies can be a combination of the nucleotide deletions discussed above with respect to each individual region.

If the adenoviral vector of the invention is deficient in a replication-essential gene function of the E2A region, the vector preferably does not comprise a complete deletion of the E2A region, which deletion preferably is less than about 230 base pairs in length. Generally, the E2A region of the adenovirus codes for a DBP (DNA binding protein), a polypeptide required for DNA replication. DBP is composed of 473 to 529 amino acids depending on the viral serotype. It is believed that DBP is an asymmetric protein that exists as a prolate ellipsoid consisting of a globular Ct with an extended Nt domain. Studies indicate that the Ct domain is responsible for DBP's ability to bind to nucleic acids, bind to zinc, and function in DNA synthesis at the level of DNA chain elongation. However, the Nt domain is believed to function in late gene expression at both transcriptional and post-transcriptional levels, is responsible for efficient nuclear localization of the protein, and also may be involved in enhancement of its own expression. Deletions in the Nt domain between amino acids 2 to 38 have indicated that this region is important for DBP function (Brough et al., *Virology*, 196: 269-281 (1993)). While deletions in the E2A region coding for the Ct region of the DBP have no effect on viral replication, deletions in the E2A region which code for amino acids 2 to 38 of the Nt domain of the DBP impair viral replication. It is preferable that any multiply replication-deficient adenoviral vector contains this portion of the E2A region of the adenoviral genome. In particular, for example, the desired portion of the E2A region to be retained is that portion of the E2A region of the adenoviral genome which is defined by the 5' end of the E2A region, specifically positions Ad5(23816) to Ad5(24032) of the E2A region of the adenoviral serotype 5 genome. This portion of the adenoviral genome desirably is included in the adenoviral vector because it is not complemented in current E2A complementing cell lines so as to provide the desired level of viral propagation.

While the above-described deletions are described with respect to an adenovirus serotype 5 genome, one of ordinary skill in the art can determine the nucleotide coordinates of the same regions of other adenovirus serotypes, such as an adenovirus serotype 2 genome, without undue experimentation, based on the similarity between the genomes of various adenovirus serotypes, particularly adenovirus serotypes 2 and 5.

In one embodiment of the invention, the adenoviral vector can comprise an adenoviral genome deficient in one or more replication-essential gene functions of each of the E1 and E4 regions (i.e., the adenoviral vector is an E1/E4-deficient adenoviral vector), preferably with the entire coding region of the E4 region having been deleted from the adenoviral genome. In other words, all the open reading frames (ORFs) of the E4 region have been removed. Most preferably, the adenoviral vector is rendered replication-deficient by deletion of all of the E1 region and by deletion of a portion of the E4 region. The E4 region of the adenoviral vector can retain the native E4 promoter, polyadenylation sequence, and/or the right-side inverted terminal repeat (ITR).

It should be appreciated that the deletion of different regions of the adenoviral vector can alter the immune response of the mammal. In particular, deletion of different regions can reduce the inflammatory response generated by the adenoviral vector. An adenoviral vector deleted of the entire E4 region can elicit a lower host immune response. Furthermore, the adenoviral vector's coat protein can be modified so as to decrease the adenoviral vector's ability or inability to be recognized by a neutralizing antibody directed against the wild-type coat protein, as described in International Patent Application WO 98/40509. Such modifications are useful for long-term treatment of persistent disorders.

The adenoviral vector, when multiply replication-deficient, especially in replication-essential gene functions of the E1 and E4 regions, can include a spacer sequence to provide viral growth in a complementing cell line similar to that achieved by singly replication-deficient adenoviral vectors, particularly an E1-deficient adenoviral vector. In a preferred E4-deficient adenoviral vector of the invention wherein the L5 fiber region is retained, the spacer is desirably located between the L5 fiber region and the right-side ITR. More preferably in such an adenoviral vector, the E4 polyadenylation sequence alone or, most preferably, in combination with another sequence exists between the L5 fiber region and the right-side ITR, so as to sufficiently separate the retained L5 fiber region from the right-side ITR, such that viral production of such a vector approaches that of a singly replication-deficient adenoviral vector, particularly a singly replication-deficient E1 deficient adenoviral vector.

The spacer sequence can contain any nucleotide sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer sequence can be coding or non-coding and native or non-native with respect to the adenoviral genome, but does not restore the replication-essential function to the deficient region. The spacer can also contain a promoter-variable expression cassette. More preferably, the spacer comprises an additional polyadenylation sequence and/or a passenger gene. Preferably, in the case of a spacer inserted into a region deficient for E4, both the E4 polyadenylation sequence and the E4 promoter of the adenoviral genome or any other (cellular or viral) promoter remain in the vector. The spacer is located between the E4 polyadenylation site and the E4 promoter, or, if the E4 promoter is not present in the vector, the spacer is proximal to the right-side ITR. The spacer can comprise any suitable polyadenylation sequence. Examples of suitable polyadenylation sequences include synthetic optimized sequences, BGH (Bovine Growth Hormone), polyoma virus, TK (Thymidine Kinase), EBV (Epstein Barr Virus) and the papillomaviruses, including human papillomaviruses and BPV (Bovine Papilloma Virus). Preferably, particularly in the E4 deficient region, the spacer includes an SV40 polyadenylation sequence. The SV40 polyadenylation sequence allows for higher virus production levels of multiply replication deficient adenoviral vectors. In the absence of a spacer, production of fiber protein and/or viral growth of the multiply replication-deficient adenoviral vector is reduced by comparison to that of a singly replication-deficient adenoviral vector. However, inclusion of the spacer in at least one of the deficient adenoviral regions, preferably the E4 region, can counteract this decrease in fiber protein production and viral growth. Ideally, the spacer is composed of the glucuronidase gene. The use of a spacer in an adenoviral vector is further described in, for example, U.S. Pat. No. 5,851,806 and International Patent Application Publication WO 97/21826.

It has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others, as described in for example, U.S. Pat. Nos. 6,225,113, 6,649,373, and 6,660,521, and International Patent Application Publication WO 00/34496. In view of the above, a replication-deficient adenoviral vector (e.g., the at least E4-deficient adenoviral vector) or a second expression vector can comprise a nucleic acid sequence encoding a trans-acting factor that modulates the persistence of expression of the nucleic acid sequence. Persistent expression of antigenic DNA can be desired when generating immune tolerance.

Desirably, the adenoviral vector requires, at most, complementation of replication-essential gene functions of the E1, E2A, and/or E4 regions of the adenoviral genome for replication (i.e., propagation). However, the adenoviral genome can be modified to disrupt one or more replication-essential gene functions as desired by the practitioner, so long as the adenoviral vector remains deficient and can be propagated using, for example, complementing cells and/or exogenous DNA (e.g., helper adenovirus) encoding the disrupted replication-essential gene functions. In this respect, the adenoviral vector can be deficient in replication-essential gene functions of only the early regions of the adenoviral genome, only the late regions of the adenoviral genome, both the early and late regions of the adenoviral genome, or all adenoviral genes (i.e., a high capacity adenovector (HC-Ad), see Morsy et al., *Proc. Natl. Acad. Sci. USA*, 95: 965-976 (1998), Chen et al., *Proc. Natl. Acad. Sci. USA*, 94: 1645-1650 (1997), and Kochanek et al., *Hum. Gene Ther.*, 10: 2451-2459 (1999)). Suitable replication-deficient adenoviral vectors, including singly and multiply replication-deficient adenoviral vectors, are disclosed in U.S. Pat. Nos. 5,837,511, 5,851,806, 5,994,106, 6,127,175, and 6,482,616; U.S. Patent Application Publications 2001/

0043922 A1, 2002/0004040 A1, 2002/0031831 A1, 2002/0110545 A1, and 2004/0161848 A1; and International Patent Application Publications WO 94/28152, WO 95/02697, WO 95/16772, WO 95/34671, WO 96/22378, WO 97/12986, WO 97/21826, and WO 03/022311.

By removing all or part of, for example, the E1, E3, and E4 regions of the adenoviral genome, the resulting adenoviral vector is able to accept inserts of exogenous nucleic acid sequences while retaining the ability to be packaged into adenoviral capsids. The nucleic acid sequence can be positioned in the E1 region, the E3 region, or the E4 region of the adenoviral genome. Indeed, the nucleic acid sequence can be inserted anywhere in the adenoviral genome so long as the position does not prevent expression of the nucleic acid sequence or interfere with packaging of the adenoviral vector.

If the adenoviral vector is not replication-deficient, ideally the adenoviral vector is manipulated to limit replication of the vector to within a target tissue. The adenoviral vector can be a conditionally-replicating adenoviral vector, which is engineered to replicate under conditions pre-determined by the practitioner. For example, replication-essential gene functions, e.g., gene functions encoded by the adenoviral early regions, can be operably linked to an inducible, repressible, or tissue-specific transcription control sequence, e.g., promoter. In this embodiment, replication requires the presence or absence of specific factors that interact with the transcription control sequence. In autoimmune disease treatment, it can be advantageous to control adenoviral vector replication in, for instance, lymph nodes, to obtain continual antigen production and control immune cell production. Conditionally-replicating adenoviral vectors are described further in U.S. Pat. No. 5,998,205.

In addition to modification (e.g., deletion, mutation, or replacement) of adenoviral sequences encoding replication-essential gene functions, the adenoviral genome can contain benign or non-lethal modifications, i.e., modifications which do not render the adenovirus replication-deficient, or, desirably, do not adversely affect viral functioning and/or production of viral proteins, even if such modifications are in regions of the adenoviral genome that otherwise contain replication-essential gene functions. Such modifications commonly result from DNA manipulation or serve to facilitate expression vector construction. For example, it can be advantageous to remove or introduce restriction enzyme sites in the adenoviral genome. Such benign mutations often have no detectable adverse effect on viral functioning. For example, the adenoviral vector can comprise a deletion of nucleotides 10,594 and 10,595 (based on the adenoviral serotype 5 genome), which are associated with VA-RNA-1 transcription, but the deletion of which does not prohibit production of VA-RNA-1.

Similarly, the coat protein of a viral vector, preferably an adenoviral vector, can be manipulated to alter the binding specificity or recognition of a virus for a viral receptor on a potential host cell. For adenovirus, such manipulations can include deletion of regions of the fiber, penton, or hexon, insertions of various native or non-native ligands into portions of the coat protein, and the like. Manipulation of the coat protein can broaden the range of cells infected by the adenoviral vector or enable targeting of the adenoviral vector to a specific cell type.

For example, in one embodiment, the adenoviral vector comprises a chimeric coat protein (e.g., a fiber, hexon pIX, pIIIa, or penton protein), which differs from the wild-type (i.e., native) coat protein by the introduction of a normative amino acid sequence, preferably at or near the carboxyl terminus. Preferably, the normative amino acid sequence is inserted into or in place of an internal coat protein sequence. One of ordinary skill in the art will understand that the normative amino acid sequence can be inserted within the internal coat protein sequence or at the end of the internal coat protein sequence. The non-native amino acid sequence of the chimeric adenoviral coat protein allows an adenoviral vector comprising the chimeric adenoviral coat protein to bind and, desirably, infect host cells not naturally infected by the corresponding adenovirus without the non-native amino acid sequence (i.e., host cells not infected by the corresponding wild-type adenovirus), to bind to host cells naturally infected by the corresponding adenovirus with greater affinity than the corresponding adenovirus without the non-native amino acid sequence, or to bind to particular target cells with greater affinity than non-target cells. By "preferentially binds" is meant that the non-native amino acid sequence binds a receptor, such as, for instance, $\alpha_v\beta_3$ integrin, with at least about 3-fold greater affinity (e.g., at least about 5-fold, 10-fold, 15-fold, 20-fold, 25-fold, 35-fold, 45-fold, or 50-fold greater affinity) than the non-native ligand binds a different receptor, such as, for instance, $\alpha_v\beta_1$ integrin.

Desirably, the adenoviral vector comprises a chimeric coat protein comprising a non-native amino acid sequence that confers to the chimeric coat protein the ability to bind to an immune cell more efficiently than a wild-type adenoviral coat protein. In particular, the adenoviral vector can comprise a chimeric adenoviral fiber protein comprising a non-native amino acid sequence which facilitates uptake of the adenoviral vector by immune cells, preferably antigen presenting cells, such as dendritic cells, monocytes, and macrophages. In a preferred embodiment, the adenoviral vector comprises a chimeric fiber protein comprising an amino acid sequence (e.g., a non-native amino acid sequence) comprising an RGD motif including, but not limited to, CRGDC (SEQ ID NO: 1), CXCRGDCXC (SEQ ID NO: 2), wherein X represents any amino acid, and CDCRGDCFC (SEQ ID NO: 3), which increases transduction efficiency of an adenoviral vector into dendritic cells. The RGD-motif, or any non-native amino acid sequence ligand, preferably is inserted into the adenoviral fiber knob region, ideally in an exposed loop of the adenoviral knob, such as the HI loop. A non-native amino acid sequence also can be appended to the C-terminus of the adenoviral fiber protein, optionally via a spacer sequence.

Where dendritic cells are the desired target cell, the non-native amino acid sequence can recognize a protein typically found on dendritic cell surfaces such as adhesion proteins, chemokine receptors, complement receptors, co-stimulation proteins, cytokine receptors, high level antigen presenting molecules, homing proteins, marker proteins, receptors for antigen uptake, signaling proteins, virus receptors, etc. Examples of such potential ligand-binding sites in dendritic cells include $\alpha_v\beta_3$ integrins, $\alpha_v\beta_5$ integrins, 2A1, 7-TM receptors, CD1, CD11a, CD11b, CD11c, CD21, CD24, CD32, CD4, CD40, CD44 variants, CD46, CD49d, CD50, CD54, CD58, CD64, ASGPR, CD80, CD83, CD86, E-cadherin, integrins, M342, MHC-I, MHC-II, MIDC-8, MMR, OX62, p200-MR6, p55, S100, TNF-R, etc. Preferably, where dendritic cells are targeted, the ligand recognizes the CD40 cell surface protein, such as, for example, a CD-40 (bi)specific antibody fragment or a domain derived from the CD40L polypeptide.

Where macrophages are the desired target, the non-native amino acid sequence can recognize a protein typically found on macrophage cell surfaces, such as phosphatidylserine receptors, vitronectin receptors, integrins, adhesion receptors, receptors involved in signal transduction and/or inflammation, markers, receptors for induction of cytokines, or receptors up-regulated upon challenge by pathogens, members of the group B scavenger receptor cysteine-rich (SRCR) superfamily, sialic acid binding receptors, members of the Fc receptor family, B7-1 and B7-2 surface molecules, lymphocyte receptors, leukocyte receptors, antigen presenting molecules, and the like. Examples of suitable macrophage surface target proteins include, but are not limited to, heparin sulfate proteoglycans, $\alpha_v\beta_3$ integrins, $\alpha_v\beta_5$ integrins, B7-1, B7-2, CD11c, CD13, CD16, CD163, CD1a, CD22, CD23, CD29, Cd32, CD33, CD36, CD44, CD45, CD49e, CD52, CD53, CD54, CD71, CD87, CD9, CD98, Ig receptors, Fc receptor proteins (e.g., subtypes of Fcα, Fcγ, Fcε, etc.), folate receptor b, HLA Class I, Sialoadhesin, siglec-5, and the toll-like receptor-2 (TLR2).

Where B-cells are the desired target, the ligand can recognize a protein typically found on B-cell surfaces, such as integrins and other adhesion molecules, complement receptors, interleukin receptors, phagocyte receptors, immunoglobulin receptors, activation markers, transferrin receptors, members of the scavenger receptor cysteine-rich (SRCR) superfamily, growth factor receptors, selectins, MHC molecules, TNF-receptors, and TNF-R associated factors. Examples of typical B-cell surface proteins include β-glycan, B cell antigen receptor (BAC), B7-2, B-cell receptor (BCR), C3d receptor, CD1, CD18, CD19, CD20, CD21, CD22, CD23, CD35, CD40, CD5, CD6, CD69, CD69, CD71, CD79a/CD79b dimer, CD95, endoglin, Fas antigen, human Ig receptors, Fc receptor proteins (e.g., subtypes of Fcα, Fcg, Fcε, etc.), IgM, gp200-MR6, Growth Hormone Receptor (GH-R), ICAM-1, ILT2, CD85, MHC class I and H molecules, transforming growth factor receptor (TGF-R), $\alpha_4\beta_7$ integrin, and $\alpha_v\beta_3$ integrin.

In another embodiment of the invention, the adenoviral vector comprises a chimeric virus coat protein not selective for a specific type of eukaryotic cell. The chimeric coat protein differs from the wild-type coat protein by an insertion of a normative amino acid sequence into or in place of an internal coat protein sequence. In this embodiment, the chimeric adenovirus coat protein efficiently binds to a broader range of eukaryotic cells than a wild-type adenovirus coat, such as described in International Patent Application WO 97/20051.

Specificity of binding of an adenovirus to a given cell also can be adjusted by use of an adenovirus comprising a short-shafted adenoviral fiber gene, as discussed in U.S. Pat. No. 5,962,311. Use of an adenovirus comprising a short-shafted adenoviral fiber gene reduces the level or efficiency of adenoviral fiber binding to its cell-surface receptor and increases adenoviral penton base binding to its cell-surface receptor, thereby increasing the specificity of binding of the adenovirus to a given cell. Alternatively, use of an adenovirus comprising a short-shafted fiber enables targeting of the adenovirus to a desired cell-surface receptor by the introduction of a normative amino acid sequence either into the penton base or the fiber knob.

The ability of an adenoviral vector to recognize a potential host cell can be modulated without genetic manipulation of the coat protein, i.e., through use of a bi-specific molecule. For instance, complexing an adenovirus with a bispecific molecule comprising a penton base-binding domain and a domain that selectively binds a particular cell surface binding site enables the targeting of the adenoviral vector to a particular cell type. Likewise, an antigen can be conjugated to the surface of the adenoviral particle through non-genetic means.

A non-native amino acid sequence can be conjugated to any of the adenoviral coat proteins to form a chimeric adenoviral coat protein. Therefore, for example, a non-native amino acid sequence can be conjugated to, inserted into, or attached to a fiber protein, a penton base protein, a hexon protein, proteins IX, VI, or IIIa, etc. The sequences of such proteins, and methods for employing them in recombinant proteins, are well known in the art (see, e.g., U.S. Pat. Nos. 5,543,328; 5,559,099; 5,712,136; 5,731,190; 5,756,086; 5,770,442; 5,846,782; 5,962,311; 5,965,541; 5,846,782; 6,057,155; 6,127,525; 6,153,435; 6,329,190; 6,455,314; 6,465,253; 6,576,456; 6,649,407; 6,740,525, and International Patent Application Publications WO 96/07734, WO 96/26281, WO 97/20051, WO 98/07877, WO 98/07865, WO 98/40509, WO 98/54346, WO 00/15823, WO 01/58940, and WO 01/92549). The chimeric adenoviral coat protein can be generated using standard recombinant DNA techniques known in the art. Preferably, the nucleic acid sequence encoding the chimeric adenoviral coat protein is located within the adenoviral genome and is operably linked to a promoter that regulates expression of the coat protein in a wild-type adenovirus. Alternatively, the nucleic acid sequence encoding the chimeric adenoviral coat protein is located within the adenoviral genome and is part of an expression cassette which comprises genetic elements required for efficient expression of the chimeric coat protein.

The coat protein portion of the chimeric adenovirus coat protein can be a full-length adenoviral coat protein to which the ligand domain is appended, or it can be truncated, e.g., internally or at the C- and/or N-terminus. However modified (including the presence of the non-native amino acid), the chimeric coat protein preferably is able to incorporate into an adenoviral capsid. Where the non-native amino acid sequence is attached to the fiber protein, preferably it does not disturb the interaction between viral proteins or fiber monomers. Thus, the non-native amino acid sequence preferably is not itself an oligomerization domain, as such can adversely interact with the trimerization domain of the adenovirus fiber. Preferably the non-native amino acid sequence is added to the virion protein, and is incorporated in such a manner as to be readily exposed to a substrate, cell surface-receptor, or immune cell (e.g., at the N- or C-terminus of the adenoviral protein, attached to a residue facing a substrate, positioned on a peptide spacer, etc.) to maximally expose the non-native amino acid sequence. Ideally, the non-native amino acid sequence is incorporated into an adenoviral fiber protein at the C-terminus of the fiber protein (and attached via a spacer) or incorporated into an exposed loop (e.g., the HI loop) of the fiber to create a chimeric coat protein. Where the non-native amino acid sequence is attached to or replaces a portion of the penton base, preferably it is within the hypervariable regions to ensure that it contacts the substrate, cell surface receptor, or immune cell. Where the non-native amino acid sequence is attached to the hexon, preferably it is within a hypervariable region (Miksza et al., *J. Virol.*, 70(3): 1836-44 (1996)). Where the non-native amino acid is attached to or replaces a portion of pIX, preferably it is within the C-terminus of pIX. Use of a spacer sequence to extend the non-native amino acid sequence away from the surface of the adenoviral particle can be advantageous in that the non-native amino acid sequence can be more available for binding to a receptor, and any steric interactions between the non-native amino acid sequence and the adenoviral fiber monomers can be reduced.

Binding affinity of a non-native amino acid sequence to a cellular receptor can be determined by any suitable assay, a variety of which assays are known and are useful in selecting a non-native amino acid sequence for incorporating into an adenoviral coat protein. Desirably, the transduction levels of host cells are utilized in determining relative binding efficiency. Thus, for example, host cells displaying $\alpha v\beta 3$ integrin on the cell surface (e.g., MDAMB435 cells) can be exposed to an adenoviral vector comprising the chimeric coat protein and the corresponding adenovirus without the non-native amino acid sequence, and then transduction efficiencies can be compared to determine relative binding affinity. Similarly, both host cells displaying $\alpha v\beta 3$ integrin on the cell surface (e.g., MDAMB435 cells) and host cells displaying predominantly $\alpha v\beta 1$ on the cell surface (e.g., 293 cells) can be exposed to the adenoviral vectors comprising the chimeric coat protein, and then transduction efficiencies can be compared to determine binding affinity.

In other embodiments (e.g., to facilitate purification or propagation within a specific engineered cell type), a non-native amino acid (e.g., ligand) can bind a compound other than a cell-surface protein. Thus, the ligand can bind blood- and/or lymph-borne proteins (e.g., albumin), synthetic peptide sequences such as polyamino acids (e.g., polylysine, polyhistidine, etc.), artificial peptide sequences (e.g., FLAG), and RGD peptide fragments (Pasqualini et al., *J. Cell. Biol.,* 130: 1189 (1995)). A ligand can even bind non-peptide substrates, such as plastic (e.g., Adey et al., *Gene,* 156: 27 (1995)), biotin (Saggio et al., *Biochem. J.,* 293: 613 (1993)), a DNA sequence (Cheng et al., *Gene,* 171: 1 (1996), and Krook et al., *Biochem. Biophys., Res. Commun.,* 204: 849 (1994)), streptavidin (Geibel et al., *Biochemistry,* 34: 15430 (1995), and Katz, *Biochemistry,* 34: 15421 (1995)), nitrostreptavidin (Balass et al., *Anal. Biochem.,* 243: 264 (1996)), heparin (Wickham et al., *Nature Biotechnol.,* 14: 1570-73 (1996)), and other substrates.

Suitable modifications to an adenoviral vector are described in U.S. Pat. Nos. 5,543,328, 5,559,099, 5,712,136, 5,731,190, 5,756,086, 5,770,442, 5,846,782, 5,871,727, 5,885,808, 5,922,315, 5,962,311, 5,965,541, 6,057,155, 6,127,525, 6,153,435, 6,329,190, 6,455,314, 6,465,253, 6,576,456, 6,649,407, 6,740,525; U.S. Patent Application Publications 20010047081, 20020013286, 20020151027 20030022355 20030099619, 20030166286, and 20040161848; and International Patent Application Publications WO 95/02697, WO 95/16772, WO 95/34671, WO 96/07734, WO 96/22378, WO 96/26281, WO 97/20051, WO 98/07865, WO 98/07877, WO 98/40509, WO 98/54346, WO 00/15823, WO 01/58940, and WO 01/92549. Similarly, it will be appreciated that numerous adenoviral vectors are available commercially. Construction of adenoviral vectors is well understood in the art. Adenoviral vectors can be constructed and/or purified using methods known in the art (e.g., using complementing cell lines, such as the 293 cell line, Per.C6 cell line, or 293-ORF6 cell line) and methods set forth, for example, in U.S. Pat. Nos. 5,965,358, 5,994,128, 6,033,908, 6,168,941, 6,329,200, 6,383,795, 6,440,728, 6,447,995, 6,475,757, and 6,908,762; U.S. Patent Application Publication 2002/0034735 A1; and International Patent Application Publications WO 98/53087, WO 98/56937, WO 99/15686, WO 99/54441, WO 00/12765, WO 01/77304, and WO 02/29388, as well as the other references identified herein.

The term "pathogen," as used herein, refers to any microorganism that causes disease. Examples of suitable pathogens include bacteria, viruses, parasites, fungi, protozoa, and prions. Suitable viruses include, but not limited to, a virus from any of the following viral families: *Arenaviridae, Arterivirus, Astroviridae, Baculoviridae, Badnavirus, Barnaviridae, Birnaviridae, Bromoviridae, Bunyaviridae* (e.g., hantavirus), *Caliciviridae, Capillovirus, Carlavirus, Caulimovirus, Circoviridae, Closterovirus, Comoviridae, Coronaviridae* (e.g., Coronavirus, such as severe acute respiratory syndrome (SARS) virus), *Corticoviridae, Cystoviridae, Deltavirus, Dianthovirus, Enamovirus, Filoviridae* (e.g., Marburg virus and Ebola virus (e.g., Zaire, Reston, Ivory Coast, or Sudan strain)), *Flaviviridae*, (e.g., Hepatitis C virus, Dengue virus 1, Dengue virus 2, Dengue virus 3, Dengue virus 4, tick-borne encephalitis virus (TBEV), and yellow fever virus), *Hepadnaviridae* (e.g., Hepatitis B virus), *Herpesviridae* (e.g., Human herpesvirus 1, 3, 4, 5, and 6, and Cytomegalovirus), *Hypoviridae, Iridoviridae, Leviviridae, Lipothrixviridae, Microviridae, Orthomyxoviridae* (e.g., Influenzavirus A and B), *Papovaviridae, Paramyxoviridae* (e.g., measles, mumps, human respiratory syncytial virus, and Nipah virus), *Parvoviridae, Picornaviridae* (e.g., poliovirus, rhinovirus, hepatovirus, and aphthovirus), *Poxviridae* (e.g., vaccinia virus, smallpox), *Reoviridae* (e.g., rotavirus), *Retroviridae* (e.g., lentivirus, such as human immunodeficiency virus (HIV) 1 and HIV 2), *Rhabdoviridae*, and *Totiviridae*. Particularly preferred picornaviridae include, for example, aphthovirus of any serotype, including serotypes A, O, C, SAT1, SAT2, SAT3, Asia1, which is the causative agent of foot and mouth disease (FMD). Particularly preferred retroviridae (retrovirus) include, for example, HIV of any Glade, including clades A, B, C, MN, and the like. The virus also can be a coronavirus, such as a SARS virus.

Suitable bacteria include, but are not limited to, *Actinomyces, Anabaena, Bacillus* (e.g., *Bacillus anthracis*), *Bacteroides, Bdellovibrio, Brucella, Burkholderia* (e.g., *Burkholderia pseudomallei*), *Caulobacter, Chlamydia, Chlorobium, Chromatium, Clostridium* (e.g., *Clostridium botulinum, Clostridium perfringens*), *Coxiella* (e.g., *Coxiella burnetii*), *Cytophaga, Deinococcus, Escherichia, Francisella* (e.g., *Francisella tularensis*), *Halobacterium, Heliobacter, Hyphomicrobium, Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Ricinus* (e.g., *Ricinus communis*), *Salmonella, Shigella, Spirillum, Spirochaeta, Staphylococcus, Streptococcus, Streptomyces, Sulfolobus, Thermoplasma, Thiobacillus, Treponema, Yersinia* (e.g., *Yersinia pestis*). When the pathogen is a bacterium, the bacterium preferably is a *Mycobacterium* species, such as, for example, *Mycobacterium tuberculosis*, which is the causative agent for tuberculosis (TB).

Preferably, the pathogen is a parasite. Suitable parasites include, but are not limited to, a parasite of the phylum *Sporozoa* (also referred to as phylum *Apicomplexa*), *Ciliophora, Rhizopoda*, or *Zoomastigophora*. Preferably, the pathogen is a parasite of the phylum *Sporozoa* and species *Plasmodium*. The parasite can be any suitable *Plasmodium* species, but preferably is a *Plasmodium* species that infects humans and causes malaria. Human-infecting *Plasmodium* species include *P. malariae, P. ovale, P. vivax*, and *P. falciparum. P. vivax* and *P. falciparum* are the most common, and *P. falciparum* is the most deadly, species of *Plasmodium* in human. Alternatively, the pathogen can be a species of *Plasmodium* that infects non-human animals. For example, *P. vinckei, P. chabaudi, P. yoelii*, and *P. berghei*. infect rodents, *P. knowlesi, P. cynomolgi, P. simiovale, P. fieldi, P. inui*, and *P. brasilianum* infect non-human primates. *P. gallinaceum* infects birds. In order to advance vaccine discovery, the genomes of a number of *Plasmodium* species have been sequenced. For example, the *P. falciparum* genome sequence is disclosed in Gardner et al., *Nature*, 419: 498-511 (2002). In addition, the *P. yoelii* genome sequence is disclosed in Carlton et al., *Nature*, 419: 512-519 (2002). Thus, an antigen identified using the inventive method can be sequenced and located within the *Plasmodium* genome using routine methods known in the art.

One of ordinary skill in the art will appreciate that it is not possible to correlate in vitro immunogenicity of an antigen identified by the inventive method with in vivo protection against pathogen challenge in a human without incurring a long and expensive preclinical and clinical development process. Thus, in some embodiments, the inventive method preferably is practiced in an animal model, most preferably a mouse model. The selection of an appropriate pathogen, e.g., *Plasmodium* species, on which the adenoviral vector array is based will therefore depend on the species of the animal model used. When the animal model is a mouse, the *Plasmodium* species on which the adenoviral vector array is based preferably is *P. yoelii*. Based on the similarity between the *P. yoelii* and *P. falciparum* genomes, one of ordinary skill in the art can identify *P. falciparum* orthologues of any *P. yoelii* antigens identified by the inventive method using routine methods known in the art.

In accordance with the inventive method, each of the adenoviral vectors in the adenoviral vector array comprises a nucleic acid sequence encoding a different antigen of a pathogen. An "antigen" is a molecule that induces an immune response in a mammal. An "immune response" can entail, for example, antibody production and/or the activation of immune effector cells (e.g., T cells). An antigen in the context of the invention can comprise any subunit, fragment, or epitope of any proteinaceous molecule, including a protein or peptide of viral, bacterial, parasitic, fungal, protozoan, prion, cellular, or extracellular origin, which ideally provokes an immune response in mammal, preferably leading to protective immunity. By "epitope" is meant a sequence on an antigen that is recognized by an antibody or an antigen receptor. Epitopes also are referred to in the art as "antigenic determinants."

In another embodiment, the inventive method can be used to identify one or more disease antigens in a mammal. By "disease antigen" is meant a self antigen whose presence or overexpression is indicative of a particular disease. The disease antigen can be any suitable antigen, but is preferably an antigen that is associated with cancer or an autoimmune disease. A "cancer antigen" is an antigen that is expressed by tumor cells but not normal cells, or an antigen that is expressed in normal cells but is overexpressed in tumor cells. Examples of suitable tumor antigens include, but are not limited to, β-catenin, BCR-ABL fusion protein, K-ras, N-ras, PTPRK, NY-ESO-1/LAGE-2, SSX-2, TRP2-INT2, CEA, gp100, kallikrein 4, prostate specific antigen (PSA), TRP-1/gp75, TRP-2, tyrosinase, EphA3, HER-2/neu, MUC1, p53, mdm-2, PSMA, RAGE-1, surviving, telomerase, and WT1. Other tumor antigens are known in the art and are described in, for example, The Peptide Database of T-Cell Defined Tumor Antigens, maintained by the Ludwig Institute for Cancer Research (http://www.cancerimmunity.org/statics/databases.htm), Van den Eynde et al., *Curr. Opin. Immunol.*, 9: 684-93 (1997), Houghton et al., *Curr. Opin. Immunol.*, 13: 134-140 (2001), and van de Bruggen et al., *Immunol. Rev.*, 188: 51-64 (2002). Antigens that are associated with autoimmune diseases typically are nuclear antigens, including, but not limited to, antigens derived from histones, nonhistone proteins bound to RNA, the nucleolus, and centromeres.

The term "array," as used herein, refers to a collection of molecules, compounds, cells, organisms, etc., that are arranged in an ordered manner. The array can be one-dimensional or multi-dimensional (e.g., a "matrix"). Desirably, the array contains a single type of molecule, compound, organism, etc. For example, all of the molecules in the array are proteins or nucleic acids. In the context of the invention, the array comprises two or more different adenoviral vectors, wherein each adenoviral vector comprises a nucleic acid sequence encoding a different antigen of a pathogen. Methods of generating and using DNA and protein arrays are well-known in the art and are described in, for example, Brown et al., *Nat. Genet.*, 21: 33-7 (1999), Duggan et al., *Nat. Genet.*, 21(1 Suppl): 10-4 (1999), Bubendorf, *Eur. Urol.*, 40(2): 231-8 (2001), Sakanyan, *J. Chromatogr. B. Analyt. Technol. Biomed. Life Sci.*, 815(1-2): 77-95 (2005), and Eickhoff et al., *Adv. Biochem. Eng. Biotechnol.*, 77: 103-12 (2002).

The adenoviral vector array can be prepared using any suitable method. One of ordinary skill in the art will appreciate that, in order to conduct a high-throughput analysis of hundreds of potential antigen genes, the adenoviral vector array desirably is constructed in a manner that is amenable to automation. Adenoviral vectors typically are produced using a plasmid-based system (see, e.g., International Patent Application Publication WO 99/15686 and U.S. Pat. No. 6,329,200). For example, E1/E3/E4-deleted adenoviral vectors can be generated by a plasmid-based system that utilizes the site-specific integrative recombination machinery of bacteriophage lambda, which facilitates in vitro transfer of genes from a small plasmid into a larger plasmid that contains the entire adenoviral genome, with the exception of the E1, E3 and E4 regions (i.e., adenovector plasmids). These adenovector plasmids are infectious and can be converted into adenovirus particles when grown in the appropriate complementing cell line. Such methods, however, enable the production of one only adenoviral vector at a time. Thus, for the purposes of the invention, such art-recognized methods of preparing adenoviral vectors must be adapted for high-throughput adenoviral vector construction, or alternative methods must be used.

The adenoviral vector array preferably is generated using a site-specific recombination-based cloning method which does not require standard nucleic acid digestion and ligation. An example of such a method is the Gateway™ Technology cloning system (Invitrogen Life Technologies, Carlsbad, Calif.), which relies on the well-characterized site-specific recombination process between bacteriophage λ and *E. coli* (see, e.g., Hartley et al., *Genome Res.*, 10: 1788-1795 (2000), Walhout et al., *Methods Enzym.*, 328: 575-592 (2000), and U.S. Pat. Nos. 5,888,732, 6,270,969, 6,277,608, and 6,720,140). This recombinant-based cloning technology provides for highly efficient and accurate directional cloning, and has been used for the high-throughput cloning of *P. falciparum* open reading frames (ORFs) (see Aguiar et al., *Genome Research*, 14: 2076-2082, (2004)). The Gateway™ technology allows for the transfer of DNA segments between different cloning vectors while maintaining orientation and reading frame, without the need for restriction endonucleases and ligase. Expression vectors are generated utilizing site-specific recombination between phage lambda site-specific attachment (att) sites. For example, site-specific recombination occurs between an attL site on the *E. coli* chromosome and an attR site on the lambda chromosome.

Upon lambda integration, recombination occurs between attL and attR sites to give rise to attB and attP sites, respectively (see, e.g., Landy et al., *Ann. Rev. Biochem.*, 58: 913-949 (1989)).

In the context of the invention, a nucleic acid sequence of interest (e.g., a *Plasmodium* nucleic acid sequence) is cloned in a Gateway™ "Entry" vector that is transcriptionally silent, kanamycin resistant (Km$^r$), and is flanked by two recombination sites (attL1 and attL2). The sequence of interest is then transferred to a Gateway™ "Destination" vector, which contains sequences necessary for gene expression, and is ampicillin resistant (Ap$^r$). The Destination vector also contains two recombination sites (attR1 and attR2) that flank a gene for negative selection, ccdB. Att1 and att2 sites confer directionality and specificity for recombination, so that only attL1 will react with attR1, and attL2 with attR2. The Entry vector and Destination vector are then combined, such that two recombination events occur: one between attL1 and attR1 and the other between attL2 and attR2. The product of these two recombination events is a plasmid construct comprising the nucleic acid of interest and a by-product (known as the "Donor" vector). The desired plasmid is under two forms of selection: antibiotic resistance and negative selection. Selecting for ampicillin resistance eliminates the Entry vector and the by-product, and selection against the negative selection marker eliminates the destination vector and co-integrate molecules.

In a preferred embodiment of the invention, Gateway™ Entry vectors are constructed which comprise nucleic acid sequences encoding one or more *Plasmodium* genes flanked by appropriate att site-specific recombination sites. Each Entry vector is then incubated with an adenovector Donor vector in a single well of a 96-well tissue culture plate. Each of the adenovector Donor vectors comprise a nucleic acid sequence encoding the adenoviral genome, with the exception of one or more adenoviral genome regions required for replication (i.e., so as to render the resulting adenoviral vector replication-deficient). In this regard, the adenovector Donor vectors preferably do not comprise a nucleic acid sequence encoding all or part of the E1 region and all or part of the E4 region. As discussed above, the adenovector Donor vectors also preferably do not comprise a nucleic acid sequence encoding the E3 region. Recombination between the Entry vectors and the adenovector Donor vectors preferably is catalyzed using Gateway™ technology, and products of the recombination reaction preferably are packaged into lambda phage heads in vitro. Phage lysates are then used to transduce a host cell strain that is permissive for growth of the recombinant adenovector plasmid but not the parental adenovector Donor plasmid. Any suitable host cell strain can be used. Preferably, the host cell strain is *E. coli* DH10B. Recombinant adenovector plasmids can be purified and isolated using any suitable method known in the art, such as those described in Sambrook et al., *Molecular Cloning, a Laboratory Manual*, 3$^{rd}$ edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994).

Once isolated, the recombinant adenovector plasmids generated as described above must be converted into infectious adenovirus particles and expanded to a scale suitable for antigen screening. Conversion preferably is accomplished by transfecting the recombinant adenovector plasmids into complementing cell lines used for propagation of replication-deficient adenoviral vectors. In this regard, any suitable complementing cell line can be used to convert the recombinant adenovector plasmids into recombinant adenovirus particles. Suitable complementing cell lines are known in the art and are described herein. Titers of viral particles generated by this method preferably are expanded in parallel in 96-well plates by successive passaging of the complementing cells until a cytopathic effect (CPE) is observed. Virus yields are then determined using any suitable method known in the art, such as the HPLC-based particle determination assay described in U.S. Pat. No. 6,447,995.

Once sufficient titers of recombinant adenoviral vector particles in the adenoviral vector array are produced, the inventive method further comprises contacting antigen presenting cells (APCs) with the adenoviral vector array. Antigen presenting cells are known in the art as highly specialized cells that can process antigens and display their peptide fragments on the cell surface together with molecules required for T cell activation. Antigen presenting cells can be "professional," meaning that they have both antigen-presenting and accessory (i.e., costimulatory) functions. In addition to processing antigens to peptides that are presented on MHC products (i.e., signal 1), professional APCs express additional "second signals" that mediate T-cell binding and costimulation. Examples of such second signals include intracellular adhesion molecules (e.g., ICAMs, CD50, CD54, and CD102), lymphocyte function associated antigens (e.g., CD2, CD11a, and CD58), and B7 molecules (e.g., CD80 and CD86). Any suitable primary, cultured, long-term, or immortalized APCs can be contacted with the adenoviral vector array. Suitable APCs include, for example, dendritic cells (DCs) (e.g., Langerhans' cells, interdigitating cells, follicular dendritic cells, and veiled cells), macrophages, B cells, fibroblasts, dendritic-like cells, and artificial APCs. APCs may or may not be transfected with specific immune molecules, such as human leukocyte antigen (HLA) or costimulatory molecules (e.g., HLA-A2-transfected jurkat cells or EBV-immortalized B cell lines).

Dendritic cells are found primarily in the skin and mucosal epithelium, continuously express high levels of the co-stimulatory B7 molecule, and function to present antigen to T cells. Upon recognition of infectious particles, DCs migrate through the lymphatics to the nearest lymph node, where they come into close contact with naive T cells. Unlike macrophages, DCs can recognize viral particles as non-self. In addition, DCs can present antigen via both MHC I and MHC II. Thus, DCs can activate both CD8+ and CD4+ T cells. Macrophages are part of the innate immune system and continuously phagocytose self-proteins and cells in their vicinity during normal tissue repair and aging (e.g., old red blood cells). Phagocytosed proteins are degraded and presented in the context of MHC II. In the case of infection, macrophages posses certain types of receptors that recognize differential carbohydrate patterns on foreign cells. Macrophages also have receptors for specific bacterial products such as lipopolysaccharide (LPS) (endotoxin). When these molecules bind their bacterial ligands, they stimulate the macrophages to up regulate MHC II and co-stimulatory B7, providing macrophages with strong antigen presentation properties. Stimulated macrophages produce cytokines, such as IL-1, IL-6, IL-8, IL-12, and TNF-α, that aid in antigen presentation. Unlike DCs and macrophages, B cells are uniquely adapted to bind specific soluble molecules through their cell-surface immunoglobulin. B cells ingest soluble proteins by pinocytosis and present antigen in the context of MHC-II. B cells, however, do not express co-stimulatory molecules, unless activated by helper T cells. Preferably, the antigen presenting cells are dendritic cells. Antigen presenting cells are further described in, for example, Janeway et al., eds., *Immunobiology*, 5th ed., Garland Publishing, New York, (2001).

The APCs can be contacted with the adenoviral vector array using any suitable method for transducing animal cells known in the art, such as those described in Sambrook et al., supra, and Ausubel et al., supra. Desirably, cultured APCs are added directly to the adenoviral vector array. More preferably, the adenoviral vector array is contained in a 96-well tissue culture plate, and cultured APCs can be added to each well of the 96-well plate. Whatever method is used, the APCs preferably are contacted with the adenoviral vector array under conditions wherein each different adenoviral vector transduces an APC so that the nucleic acid sequences of the different adenoviral vectors are expressed and the different antigens are produced in the APCs.

One of ordinary skill in the art will appreciate that every protein or peptide encoded by a particular pathogen does not necessarily elicit an immune response in an infected host. Thus, the invention comprises assaying the immunogenicity of the antigen produced in each APC. To this end, the APCs preferably are incubated with effector T lymphocytes obtained from a mammal immunized against the pathogen from which the nucleic acid sequences are derived. Unlike naïve T lymphocytes, effector T lymphocytes can mediate the removal of pathogens from a host without the need for further differentiation or costimulation. Effector T lymphocytes are often referred to in the art at "armed" effector T lymphocytes, because their effector function can be triggered by antigen binding alone. The three types of effector T lymphocytes, CD8, CD4 Th1, and CD4 Th2 have specificity for different kinds of pathogens. CD8 T lymphocytes (also referred to in the art as cytotoxic T lymphocytes (CTL)) kill infected cells displaying cytosolic pathogen peptides on MHC Class 1 molecules. CD4 Th1 cells activate macrophages with persistent vesicular pathogens whose peptides are displayed on MHC Class II molecules. CD4 Th1 cells also activate B cells to produce opsonizing antibodies. CD4 Th2 cells activate B cells that have internalized specific antigens and display peptides on MHC Class II molecules. Effector T lymphocytes are further described in, for example, Janeway et al., supra.

The effector T lymphocytes preferably are obtained from a mammal immunized with the pathogen from which the nucleic acid sequences encoded by the adenoviral vector array are derived. In this regard, the effector T lymphocytes are obtained from a mammal that previously has been infected with any of the pathogens described herein, such that the mammal has mounted an immune response against the pathogen. Thus, a mammal is "immunized" against a pathogen if the mammal has developed humoral immunity (i.e., antibodies) and/or cellular immunity (e.g. effector T lymphocytes) against one or more antigens of a pathogen. The effector T lymphocytes can be isolated from a mammal using any suitable method known in the art. For example, T lymphocytes can be isolated from peripheral blood from an immunized mammal (e.g., a human) by using density centrifugation over a step gradient consisting of a mixture of the carbohydrate Ficoll™ and the dense iodine-containing compound metrizamide. This results in a population of mononuclear cells, called peripheral blood mononuclear cells (PBMCs), that have been depleted of red blood cells and most polymorphonuclear leukocytes or granulocytes, and consists mainly of lymphocytes and monocytes. T lymphocytes can be isolated from PBMCs by binding a sample to antibody-coated plastic surfaces, which is known in the art as "panning," or by killing unwanted cells by treatment with a specific antibody and complement. Alternatively, PBMCs can be passed over columns of antibody- and nylon-coated steel wool, and different populations differentially eluted. Preferably, T lymphocytes are isolated from PBMCs using flow cytometry or fluorescence-activated cell sorting (FACS). Methods for isolating lymphocytes from mammals, particularly humans, are further described in Janeway et al., supra.

In nature, malaria parasites are spread by successively infecting two types of hosts: humans and female *Anopheles* mosquitoes. In this respect, malaria parasites are present as "sporozoites" in the salivary glands of the female *Anopheles* mosquito. When the *Anopheles* mosquito takes a blood meal on another human, the sporozoites are injected with the mosquito's saliva, enter the circulatory system, and within minutes of inoculation will invade a human liver cell (hepatocyte). After invading hepatocytes, the parasite undergoes asexual replication. The stage of the parasite life cycle encompassing sporozoite and liver stages typically is referred to in the art as the "pre-erythrocytic stage," the "liver stage," or "the exo-erythrocytic stage." The progeny, called "merozoites," are released into the circulatory system following rupture of the host hepatocyte. Antigens expressed during the pre-erythrocytic stage of infection include, but are not limited to, circumsporozoite protein (CSP), sporozoite surface protein 2 (SSP2), liver-stage antigen 1 (LSA-1), Pf exported protein 1 (PfExp-1)/Py hepatocyte erythrocyte protein 17 (PyHEP17), and Pf antigen 1.

Merozoites released from the infected liver cells invade erythrocytes (red blood cells). The merozoites recognize specific proteins on the surface of the erythrocyte and actively invade the cell in a manner similar to other mosquito-borne parasites. After entering the erythrocyte, the parasite undergoes a trophic period followed by asexual replication to produce successive broods of merozoites. The progeny merozoites grow inside the erythrocytes and destroy them, and are then released to initiate another round of infection. This stage of infection typically is referred to in the art as the "blood-stage" or "erythrocytic stage." Blood-stage parasites are those that cause the symptoms of malaria. When certain forms of blood-stage parasites (i.e., "gametocytes") are picked up by a female *Anopheles* mosquito during a blood meal, they start another, different cycle of growth and multiplication in the mosquito. Antigens expressed during the blood-stage of infection include, but are not limited to, merozoite surface protein 1 (MSP-1), merozoite surface protein 2 (MSP-2), erythrocyte binding antigen 175 (EBA-175), ring-infected erythrocyte surface antigen (RESA), serine repeat antigen (SERA), glycophorin binding protein (GBP-130), histidine rich protein 2 (HRP-2), rhoptry-associated proteins 1 and 2 (RAP-1 and RAP-2), erythrocyte membrane protein 1 (PfEMP1), and apical membrane antigen 1 (AMA-1). The *Plasmodium* life cycle is described in, for example, Ramasamy et al., *Med. Vet. Entomol.*, 11(3): 290-96 (1997), Hall et al., *Science*, 307 (5706): 82-86 (2005), and I. W. Sherman, ed., *Malaria: Parasite Biology, Pathogenesis, and Protection*, American Society of Microbiology (1998).

In a preferred embodiment of the invention, the effector T lymphocytes are obtained from a mammal that has been immunized with *Plasmodium* sporozoites. More preferably, the effector T lymphocytes are obtained from a mammal that has been immunized with *Plasmodium* sporozoites that have been attenuated via radiation so that the sporozoite infects the liver and undergoes partial development but does not develop to the blood-stage form. The mammal can be immunized with irradiated sporozoites obtained from any

*Plasmodium* species described herein. Most preferably, the mammal has been immunized with irradiated *P. yoelii* sporozoites.

Following incubation of the APCs with effector T lymphocytes obtained from a mammal immunized against the pathogen, the inventive method comprises screening for an immune response from the effector T lymphocytes. The immune response can be any suitable effector T lymphocyte immune response known in the art, including, but not limited to, cytokine secretion, effector T cell cytotoxicity, and immune activation of effector T cells. Preferably, the inventive method comprises screening for secretion by the effector T lymphocytes. In this regard, cytokine secretion from an effector T lymphocyte contacting an APC indicates that the effector T lymphocyte recognizes the antigen produced and displayed by the APC. Furthermore, it is well known in the art that effector T lymphocytes, such as effector helper T effector lymphocytes, secrete cytokines upon antigen recognition which promote different activities. In this regard, inflammatory or Th1 CD4 T cells produce interleukin-2 (IL-2), interferon gamma (IFNγ), and tumor necrosis factor beta (TNFβ), which activate CTLs and macrophages to stimulate cellular immunity and inflammation. Th1 CD4 T cells also secrete interleukin-3 (IL-3) and granulocyte-macrophage colony-stimulating factor (GM-CSF) to stimulate bone marrow to produce more leukocytes and signal B cells to produce opsonizing antibodies (e.g., IgG1 and IgG3 in humans and IgG2a and IgG2b in the mouse). Helper or Th2 CD4 T cells activate naïve B cells to divide and secrete IgM. Th2 CD4 cells also secrete IL-4, IL-5, and IL-6, which stimulate neutralizing antibody production by B cells. Thus, in the context of the inventive method, the effector T lymphocytes are screened for secretion of any suitable cytokine. Suitable cytokines include, but are not limited to, IFN-γ, TNF-β, TNF-α, GM-CSF, CD40 ligand, Fas ligand, and interleukins (e.g., IL-1, IL-2, IL-3, IL-4, IL-5, IL-6, and IL-10). Most preferably, the effector T lymphocytes are screened for secretion of IFN-γ. Cytokine secretion can be detected and measured using any suitable method known in the art, such as, for example, ELISPOT assays, intracellular cytokine staining assays, flow cytometry, or fluorescence-activated cell sorting (FACS) assays. In addition, effector T lymphocyte cytotoxicity can be measured using CTL assays, such as a chromium release assay (see, e.g., Walker et al., *Nature,* 328: 345-48 (1987)), and immune activation can be measured using multiparameter flow cytometry (see, e.g., Picker et al., *Blood,* 86: 1408-1419 (1995)).

The invention also provides a method of identifying an antigen from a pathogen comprising: (a) providing an adenoviral vector array comprising two or more different adenoviral vectors, wherein each adenoviral vector comprises a nucleic acid sequence encoding a different antigen of a pathogen, (b) administering each of the adenoviral vectors of the adenoviral vector array to a mammal, such that the nucleic acid sequence is expressed and the antigen is produced in the mammal, (c) infecting each mammal with the pathogen, and (d) screening the infected mammal for onset of a disease caused by the pathogen, wherein the absence in the infected mammal of a disease caused by the pathogen indicates that the adenoviral vector encodes an antigen of the pathogen, whereupon the antigen is identified. Descriptions of the adenoviral vector array and pathogen, and components thereof, set forth above in connection with other embodiments of the invention also are applicable to those same aspects of the aforesaid method.

In this embodiment, each adenoviral vector of the adenoviral vector array preferably is administered to a mammal (e.g., a human), wherein the nucleic acid sequence encoding the antigen is expressed and the antigen is produced in the mammal. In other words, only one adenoviral vector of the adenoviral vector array is administered to the mammal. Thus, in this embodiment, the analysis of a complete adenoviral vector array requires the use of multiple mammals. Desirably, each adenoviral vector is administered as part of a pharmaceutical composition comprising the adenoviral vector. Alternatively, the adenoviral vector can be administered as part of an unpurified cell lysate comprising the adenoviral vector. In this manner, adenoviral vectors are not purified from the complementing cell lines in which they are produced, but rather, an unpurified lysate of the adenovirus-infected complementing cells is administered to the mammal.

Following administration of the adenoviral vectors to the mammals, each mammal is infected with a suitable pathogen, such as those described herein. Preferably, the mammal is infected with a *Plasmodium* species, most preferably *P. falciparum* or *P. yoelii*. Infection of the mammal can be accomplished using any suitable method know in the art, such as by, for example, administration of a pharmaceutical composition comprising the pathogen itself (killed or attenuated), a nucleic acid molecule encoding the genome of the pathogen, or a live but latent form of the pathogen (e.g., *Plasmodium* sporozoites). Preferably, the mammal is infected with a live, disease-causing pathogen. Preferred administration routes include, but are not limited to, intramuscular, intravenous, intraarterial, oral, and inhalation, as described elsewhere herein.

As described herein, infection with a pathogen typically results in the onset of disease, unless the infected host has acquired protective immunity against the pathogen. Because the adenoviral vectors desirably encode at least one antigen of the pathogen that provides protective immunity against further challenge from the pathogen, the method comprises screening for onset of a disease caused by the pathogen. It will be appreciated that the absence of a disease caused by the pathogen in the mammal indicates that a particular adenoviral vector of the adenoviral vector array encodes an antigen of the pathogen which provides protective immunity to the mammal. On the other hand, the development of a disease characteristic of pathogen infection indicates that the adenoviral vector administered to the diseased mammal does not encode an antigen that contributes to protective immunity.

In accordance with the invention, once it is determined that a particular adenoviral vector of the adenoviral vector array encodes an antigen of the pathogen, as evidenced by cytokine secretion or protection from pathogen challenge, the antigen preferably is identified, e.g., by being recovered from the adenoviral vector. For example, both the nucleic acid sequence encoding the antigen and the amino acid sequence of the antigen can be determined using methods known in the art, such as those described in Sambrook et al., supra, and Ausbel et al., supra.

The invention also provides a method of inducing an immune response against a pathogen in a mammal utilizing the antigens identified as described above. The method can comprise administering to the mammal an antigen identified as described above. Alternatively, and preferably, the method comprises (a) preparing an adenoviral vector comprising a nucleic acid sequence encoding an antigen of a pathogen identified by the methods described above, and (b) administering the adenoviral vector to a mammal infected by the pathogen, wherein the antigen is expressed in the mammal to induce an immune response. Descriptions of the adenoviral vector and pathogen, and components thereof, set forth above in connection with other embodiments of the invention also are applicable to those same aspects of the aforesaid method of inducing an immune response.

In the method of the invention, the adenoviral vector preferably is administered to a mammal (e.g., a human), wherein the nucleic acid sequence encoding the antigen is expressed to induce an immune response against the antigen. The adenoviral vector comprises at least one nucleic acid sequence that encodes at least one antigen. In this respect, the adenoviral vector can encode one nucleic acid sequence that encodes multiple different antigens (e.g., 2, 3, 4, or 5, antigens), or the adenoviral vector can encode multiple nucleic acid sequences, each of which encodes a different antigen. The immune response can be a humoral immune response, a cell-mediated immune response, or, desirably, a combination of humoral and cell-mediated immunity. Ideally, the immune response provides protection upon subsequent challenge with the pathogen comprising the antigen. However, protective immunity is not required in the context of the invention. The inventive method further can be used for antibody production and harvesting.

Administering the adenoviral vector encoding the antigens can be one component of a multistep regimen for inducing an immune response in a mammal. In particular, the inventive method can represent one arm of a prime and boost immunization regimen. The inventive method, therefore, can comprise administering to the mammal a priming gene transfer vector comprising a nucleic acid sequence encoding at least one antigen prior to administering the adenoviral vector. The antigen encoded by the priming gene transfer vector can be the same or different from the antigens of the adenoviral vector. The adenoviral vector is then administered to boost the immune response to a given pathogen. More than one boosting composition comprising the adenoviral vector can be provided in any suitable timeframe (e.g., at least about 1 week, 2 weeks, 4 weeks, 8 weeks, 12 weeks, 16 weeks, or more following priming) to maintain immunity.

Any gene transfer vector can be employed as a priming gene transfer vector, including, but not limited to, a plasmid, a retrovirus, an adeno-associated virus, a vaccinia virus, a herpesvirus, an alphavirus, or an adenovirus. Ideally, the priming gene transfer vector is a plasmid, an alphavirus, or an adenoviral vector. To maximize the effect of the priming regimen, the priming gene transfer vector can comprise more than one nucleic acid sequence encoding an antigen of the pathogen. Preferably, the priming gene transfer vector comprises two or more (e.g., 2, 3, 5, or more) nucleic acid sequences each encoding an antigen of the pathogen. Alternatively, an immune response can be primed or boosted by administration of the antigen itself, e.g., an antigenic protein, intact pathogen (e.g., *Plasmodium* sporozoites), parasitized erythrocytes, inactivated pathogen, and the like.

Any route of administration can be used to deliver the adenoviral vector to the mammal. Indeed, although more than one route can be used to administer the adenoviral vector, a particular route can provide a more immediate and more effective reaction than another route. Preferably, the adenoviral vector is administered via intramuscular injection. A dose of adenoviral vector also can be applied or instilled into body cavities, absorbed through the skin (e.g., via a transdermal patch), inhaled, ingested, topically applied to tissue, or administered parenterally via, for instance, intravenous, peritoneal, or intraarterial administration.

The adenoviral vector can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the adenoviral vector. The adenoviral vector also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

The dose of adenoviral vector administered to the mammal will depend on a number of factors, including the size of a target tissue, the extent of any side-effects, the particular route of administration, and the like. The dose ideally comprises an "effective amount" of adenoviral vector, i.e., a dose of adenoviral vector which provokes a desired immune response in the mammal. The desired immune response can entail production of antibodies, protection upon subsequent challenge, immune tolerance, immune cell activation, and the like. Desirably, a single dose of adenoviral vector comprises at least about $1 \times 10^5$ particles (which also is referred to as particle units) of the adenoviral vector. The dose preferably is at least about $1 \times 10^6$ particles (e.g., about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles), and most preferably at least about $1 \times 10^9$ particles (e.g., about $1 \times 10^9$-$1 \times 10^{10}$ particles) of the adenoviral vector. The dose desirably comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ particles). In other words, a single dose of adenoviral vector can comprise, for example, about $1 \times 10^6$ particle units (pu), $2 \times 10^6$ pu, $4 \times 10^6$ pu, $1 \times 10^7$ pu, $2 \times 10^7$ pu, $4 \times 10^7$ pu, $1 \times 10^8$ pu, $2 \times 10^8$ pu, $4 \times 10^8$ pu, $1 \times 10^9$ pu, $2 \times 10^9$ pu, $4 \times 10^9$ pu, $1 \times 10^{10}$ pu, $2 \times 10^{10}$ pu, $4 \times 10^{10}$ pu, $1 \times 10^{11}$ pu, $2 \times 10^{11}$ pu, $4 \times 10^{11}$ pu, $1 \times 10^{12}$ pu, $2 \times 10^{12}$ pu, or $4 \times 10^{12}$ pu of the adenoviral vector.

The adenoviral vector desirably is administered in a composition, preferably a pharmaceutically acceptable (e.g., physiologically acceptable) composition, which comprises a carrier, preferably a pharmaceutically (e.g., physiologically) acceptable carrier and the adenoviral vector(s). Any suitable carrier can be used within the context of the invention, and such carriers are well known in the art. The choice of carrier will be determined, in part, by the particular site to which the composition is to be administered and the particular method used to administer the composition. Ideally, in the context of adenoviral vectors, the composition preferably is free of replication-competent adenovirus. The composition can optionally be sterile or sterile with the exception of the inventive adenoviral vector.

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the adenoviral vector for use in the inventive method is administered in a composition formulated to protect the expression vector from damage prior to administration. For example, the composition can be formulated to reduce loss of the adenoviral vector on devices used to prepare, store, or administer the expression vector, such as glassware, syringes, or needles. The composition can be formulated to decrease the light sensitivity and/or temperature sensitivity of the expression vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the vector, facilitate administration, and increase the efficiency of the inventive method. Formulations for adenoviral vector-containing compositions are further described in, for example, U.S. Pat. No. 6,225,289, U.S. Pat. No. 6,514,943, U.S. Patent Application Publication 2003/0153065 A1, and International Patent Application Publication WO 00/34444. A composition also can be formulated to enhance transduction efficiency. In addition, one of ordinary skill in the art will appreciate that the adenoviral vector can be present in a composition with other therapeutic or biologically-active agents. For example, factors that control inflammation, such as ibuprofen or steroids, can be part of the composition to reduce swelling and inflammation associated with in vivo administration of the viral vector. In addition, immune system stimulators can be administered to enhance any immune response to the antigen. Antibiotics, i.e., microbicides and fungicides, can be present to treat existing infection and/or reduce the risk of future infection, such as infection associated with gene transfer procedures.

The following examples further illustrate the invention but, of course, should not be construed as in any way limiting its scope.

EXAMPLE 1

This example demonstrates the preparation of an adenoviral vector array wherein each adenoviral vector comprises a nucleic acid sequence encoding a different P. yoelii antigen.

Plasmids encoding an adenoviral vector genome deficient in the E1, E3, and E4 regions were constructed using AdFlex technology (GenVec Inc., Gaithersburg, Md.), which utilizes phage lambda site-specific recombination for in vitro transfer of genes from smaller plasmid vectors to large plasmid vectors that contain the entire adenoviral genome. Several different AdFlex plasmids have been generated, all of which comprise (i) the attR1-CmR-ccB-attR2 expression cassette (Invitrogen, Inc., Carlsbad, Calif.) inserted into an E1 deletion site in between a CMV promoter and an SV40 polyadenylation site, (ii) a lambda cos site, and (iii) a LacI restriction site. Certain AdFlex plasmids also contain the p15 origin of replication, the colE1 origin of replication, and/or genes encoding resistance to kanamycin, ampicillin, or tetracycline.

The resulting adenovector plasmids were transfected into 293-ORF6 complementing cells (GenVec Inc., Gaithersburg, Md.), and infectious adenovector plasmids were rescued. Samples of infectious adenovector plasmids were added to six wells of a 96-well tissue culture plate. Gateway™ donor plasmids (pDONR) containing the nucleic acid sequences encoding P. yoelii antigens flanked by att site-specific recombination sites were generated, and incubated with the adenovector plasmids in the 96-well plate. Recombination between each adenovector plasmid and the pDONR plasmids was catalyzed via an LR reaction using Gateway™ technology (Invitrogen Life Technologies, Carlsbad, Calif.).

E. coli strain DH10B was transformed with 2 µl of the LR reaction product and grown in the presence of kanamycin. Cultures were incubated overnight at 30° C. The following day, two colonies were chosen from each culture dish for expansion. Plasmid DNA was purified from E. coli using the QIA well 8 plasmid purification kit (Qiagen, Inc., Valencia, Calif.) and linearized with PacI. Restriction digestion patterns from each of the six recombinant adenovector plasmids indicated that each colony contained only the desired recombinant adenovector plasmid, which verified that adenovector plasmids could be generated with 100% efficiency using the Gateway™ system.

The results of this example demonstrate the construction of multiple infectious recombinant adenovector plasmids in parallel format, which is suitable for automation.

EXAMPLE 2

This example demonstrates the conversion of arrayed adenovector plasmids into adenovirus particles.

Based on published reports indicating that a dose of $1 \times 10^4$ pu/cell of adenoviral vector is necessary to infect 90% of dendritic cells in vitro (Wan et al., *Hum. Gene Ther.,* 8: 1355-63 (1997), and Gahn et al., *Int. J. Cancer,* 93: 706-13 (2001)), it is estimated that $5 \times 10^8$ pu of adenovector will be necessary to practice the inventive method. The burst size for E1/E3/E4-deficient adenovectors in 293-ORF6 cells is approximately $5 \times 10^4$ pu/cell. As $2 \times 10^4$ cells can easily be seeded in a single well of a 96-well plate, it is expected that $1 \times 10^9$ particles of adenovector can be produced from a single well. This quantity of vector likely will be sufficient for the inventive APC cell-based assays for antigen identification.

293-ORF6 complementing cells are transfected using Polyfect Transfection Reagent (Qiagen, Inc., Gaithersburg, Md.) in 96-well plates. Based on extrapolations from larger scale rescue, less than $1 \times 10^4$ particles of adenovector can be rescued using this approach, as typically less than $1 \times 10^6$ particles are rescued in 293-ORF6 cells grown in 60 mm plates. Plates are incubated at 37° C. for approximately 10 days, or until complete cytopathic effect (CPE) is observed.

In the event that the above method does not yield $1 \times 10^9$ pu of adenovector required for the T cell screen, a passaging step will be performed to generate the high titer stock. In this regard, adenovector will be liberated from the 293-ORF6 cells at 3 days post-transfection by three freeze-thaw cycles, and the cell lysates will be used to infect new cells in 96-well plates. The vector titers are expanded in parallel in 96-well plates by successive passaging until CPE is observed. Vector yields will be determined by a HPLC-based particle determination assay, and active virus particles will be quantified by using the focal forming unit assay described in, for example, Cleghon et al., *Virology,* 197: 564-575 (1993).

The protocol of this example can be used to demonstrate the conversion of arrayed recombinant adenovector plasmids into adenovirus particles at a scale suitable for antigen screening.

EXAMPLE 3

This example demonstrates the ability of antigen presenting cells transduced with an adenoviral vector encoding an antigen of a pathogen to recall cellular immune responses from mice immunized with the pathogen.

Cells from the A2/20J (A20) dendritic cell line were transduced with an E1/E3/E4-deficient Ad5 vector encoding the *P. yoelii* CSP protein (AdPyCSP) at a multiplicity of infection (MOI) of 10, 1, or 0.1 using methods known in the art. As a positive control, A20 cells were transfected with a plasmid encoding PyCSP, or a recombinant pox vector encoding PyCSP (PyCSP-COPAC) at an MOI of 10. Negative controls included A20 cells transfected with an empty plasmid or parental vaccinia virus at an MOI of 10, and A20 cells transduced with an adenoviral vector encoding green fluorescent protein (GFP) at an MOI of 10, 1, or 0.1.

Transduced A20 cells were plated at $1 \times 10^5$ cells per well in 96-well plates. Splenocytes from BALB/c mice immunized with irradiated *P. yoelii* sporozoites were incubated with the transduced A20 cells in the 96-well plates. After a 36 hour incubation, IFN-γ levels were measured by ELISpot, as it is widely considered that IFN-γ is the most appropriate in vitro marker of pre-erythrocytic stage protection (Doolan et al., *J. Immunol.*, 163: 884-92 (1999), and Doolan et al., *J. Immunol.*, 165: 1453-62 (2000)). Spots were read using a CTL automated reader.

A20 cells transduced with AdPyCSP efficiently recalled PyCSP antigen-specific T cell responses in vitro following infection at an MOI of 10. At an MOI of 1 there was a decrease in the number of T cells stimulated to secrete IFN-γ, and at an MOI of 0.1 no PyCSP specific T cell responses were observed. Greater than 400 cells per million spleen cells produced IFN-γ in response to A20 cells infected with PyCSP-COPAC, or A20 cells transfected with PyCSP plasmid. A20 cells infected at an MOI of 10 with Ad5 PyCSP stimulated more than 300 cells per million responder spleen cells to produce IFN-γ. At lower MOIs, there was a rapid drop in the number of cells producing IFN-γ.

The results of this example demonstrate that APCs transduced with adenovectors encoding *Plasmodium* antigens can recall cellular immune responses in *Plasmodium*-immunized mice.

EXAMPLE 4

This example demonstrates the ability of antigen presenting cells infected with the adenoviral vector array of the invention to induce a protective immune response in vitro.

Primary dendritic cells (DC) and the A2/20J (A20) dendritic cell line are transformed with the adenoviral vectors produced in Example 1 by incubating separate 96-well plates containing the six adenoviral vectors produced in Example 1 with either primary DC or A20 cells using methods known in the art. Effector T lymphocytes are obtained by harvesting spleens from BALB/c mice immunized with irradiated *P. yoelii* sporozoites. These splenocytes are considered to contain sporozoite-immune effector T cell populations, which recognize protective target antigens.

The adenovector-transduced APCs are co-cultured with autologous lymphocytes for defined periods of time from 24 to 96 hours after transduction to assay for cellular immune responses. IFN-γ levels are measured using ELIspot, flow cytometry, or FACS-based assays.

The protocol set out in this example can be used to confirm the ability of the inventive method to identify antigens that induce protective immunity against *Plasmodium* infection.

EXAMPLE 5

This example demonstrates the ability of antigen presenting cells infected with the adenoviral vector array of the invention to induce a protective immune response in vivo.

Mice are immunized with E1/E3/E4-deficient adenoviral vectors encoding PyCSP, PyHEP17, or three novel Py antigens twice at 6 week intervals. Alternatively, a DNA prime/adenovector boost immunization schedule is used. Mice are then challenged with infectious *P. yoelii* sporozoites, and the capacity of the antigen to confer complete or partial protection against parasite challenge is assessed. Sterile protection is indicated by complete absence of blood-stage parasitemia (see, e.g., Doolan et al., *J. Immunol.*, 163: 884-92 (1999), Sedegah et al., *Proc. Natl. Acad. Sci. USA*, 91: 9866-70 (1994), and Doolan et al., *J. Exp. Med.*, 184: 1739-46 (1996)). Partial protection is indicated by reduction in liver-stage parasite burden, as evaluated by qRT-PCR (see Witney et al., *Mol. Biochem. Parasitol.*, 118: 233-45 (2001)). In vitro immune reactivity, as assayed by IFN-γ, ELISpot, or FACS-based assays (described in Example 4), then is correlated with in vivo protective capacity, as evaluated by a decrease in liver-stage and/or blood-stage parasite burden.

The protocol of this example can be used to demonstrate that antigens identified using the inventive method are capable of protecting against parasite challenge in vivo.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of identifying an antigen from a pathogen, which method comprises
   (a) providing an adenoviral vector array comprising two or more different adenoviral vectors, wherein each adenoviral vector comprises a nucleic acid sequence encoding a different antigen of a pathogen,
   (b) administering each of the adenoviral vectors of the adenoviral vector array to a separate mammal, such that the nucleic acid sequence is expressed and the antigen is produced in the mammal,
   (c) infecting each mammal with the pathogen, and
   (d) screening the infected mammal for onset of a disease caused by the pathogen, wherein the absence in the infected mammal of a disease caused by the pathogen indicates that the adenoviral vector encodes an antigen of the pathogen, whereupon the antigen is identified.

2. The method of claim 1, wherein the pathogen is *Plasmodium* species.

3. The method of claim 2, wherein the pathogen is selected from the group consisting of *Plasmodium berghei, Plasmodium chabaudi, Plasmodium vinckei, Plasmodium yoelii, Plasmodium falciparum, Plasmodium vivax, Plasmodium malariae,* and *Plasmodium ovale.*

4. The method of claim 1, wherein the adenoviral vector is administered as part of an unpurified cell lysate comprising the adenoviral vector.

5. The method of any of claims 1-4, wherein the mammal is a mouse.

6. The method of any of claims 1-4, wherein the mammal is a human.

* * * * *

SEQUENCE LISTING

<160> NUMBER OF SEQ ID NOS: 3

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Cys Arg Gly Asp Cys
1               5

<210> SEQ ID NO 2
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: "Xaa" may be any amino acid
<220> FEATURE:
<221> NAME/KEY: MISC_FEATURE
<222> LOCATION: (8)..(8)
<223> OTHER INFORMATION: "Xaa" may be any amino acid

<400> SEQUENCE: 2

Cys Xaa Cys Arg Gly Asp Cys Xaa Cys
1               5

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Cys Asp Cys Arg Gly Asp Cys Phe Cys
1               5